US005645855A

United States Patent [19]
Lorenz

[11] Patent Number: 5,645,855
[45] Date of Patent: Jul. 8, 1997

[54] ADHESIVE COMPOSITIONS INCLUDING POLYVINYLPYRROLIDONE ACRYLIC ACID POLYMERS, AND POLYAMINES

[75] Inventor: Donald H. Lorenz, Basking Ridge, N.J.

[73] Assignee: Ridge Scientific Enterprises, Inc., Basking Ridge, N.J.

[21] Appl. No.: 615,624

[22] Filed: Mar. 13, 1996

[51] Int. Cl.$^6$ .......................... A61M 37/00; A61K 9/10; C09J 9/02; C09J 139/06

[52] U.S. Cl. .................. 424/449; 424/448; 424/487; 514/944; 602/52; 602/54; 604/307; 252/315.4; 156/331.2; 206/813

[58] Field of Search ................................ 424/448, 449, 424/487; 514/944; 602/52, 54; 156/331.2; 252/315.4

[56] References Cited

U.S. PATENT DOCUMENTS

| | | | |
|---|---|---|---|
| 4,906,475 | 3/1990 | Kim | 424/448 |
| 5,306,504 | 4/1994 | Lorenz | 424/449 |

*Primary Examiner*—Edward J. Webman
*Attorney, Agent, or Firm*—John G. Gilfillan; Elliot M. Olstein; Raymond J. Lillie

[57] ABSTRACT

A composition comprising a cross-linked salt of (a) a polyvinylpyrrolidone having ring opened pyrrolidone groups; (b) at least one acrylic acid-containing or methacrylic acid-containing polymer; and (c) an amine-containing polymer. The composition may be used as a pressure-sensitive adhesive, has good tack, and may be peeled from the body or from an object without causing damage or injury to the body or object.

26 Claims, No Drawings

ADHESIVE COMPOSITIONS INCLUDING POLYVINYLPYRROLIDONE ACRYLIC ACID POLYMERS, AND POLYAMINES

This invention relates to adhesives and, in particular, to hydrogel pressure-sensitive adhesives. More particularly, this invention relates to adhesives which include a polyvinylpyrrolidone, an acrylic acid polymer, and a polyamine. Such adhesives contain only a minimum of water, yet do not dry out.

Pressure-sensitive adhesives have a variety of applications, including uses in wound and burn dressings, bandages, surgical drapes, plasters, transdermal drug delivery systems, antimicrobial barriers for catheter hubs, and ostomy products.

Where the pressure sensitive hydrogel also contains electrolyte that imparts conductivity, the pressure sensitive hydrogel can be used for electrodes, for anti-static closure strips for electronic packaging, anti-static sticky mats for clean rooms, and for attaching photographic or X-ray film to spindles of film canisters.

U.S. Pat. No. 5,306,504 discloses an adhesive hydrogel composition having a high water content, and which comprises a cross-linked ampholytic salt of a high molecular weight water-soluble polyvinylpyrrolidone having ring opened pyrrolidone groups, and a water-soluble amine-containing polymer. The polyvinylpyrrolidone has ring opened pyrrolidone groups providing at least $1.5 \times 10^{-2}$ milliequivalents of carboxylic acid groups per gram of polymer. The amine-containing polymer may be polyethyleneimine, amine-terminated polyethyleneoxide, or amine-terminated polyethylene oxide/polypropylene oxide.

Such an adhesive, however, has a tack, or a stickiness, which is less than that desired for certain applications, such as, for example, as a wound dressing for moist or damp skin or as a closure strip for packaging of electronic components. Thus, it is an object of the present invention to provide an adhesive having an increased tack yet remain readily peelable from the body or from the object to which it is adhered, and which has improved adhesion to wet skin.

In accordance with an aspect of the present invention, there is provided a composition which comprises a cross-linked salt of (a) a polyvinylpyrrolidone having ring opened pyrrolidone groups; (b) at least one acrylic acid-containing polymer or methacrylic acid-containing polymer; and (c) an amine-containing polymer.

In one embodiment, the polyvinylpyrrolidone has ring opened pyrrolidone groups which provide at least $1.5 \times 10^{-2}$ milliequivalents of carboxylic acid groups per gram of polymer, preferably at least $1.7 \times 10^{-2}$ milliequivalents of carboxylic acid groups per gram of polymer. Higher levels of ring opened pyrrolidone groups provide a greater number of cross-links; however, the level should not be so high as to result in significant cross-linking of the polyvinylpyrrolidone with itself. Ring opening of pyrrolidone groups of the polyvinylpyrrolidone may be accomplished by means known to those skilled in the art, such as by treatment in aqueous solution at elevated temperature with a weak acid (such as acetic acid), or with a base, such as sodium hydroxide.

In a preferred embodiment, the polyvinylpyrrolidone has a high molecular weight. In one embodiment, the polyvinylpyrrolidone has a K-value of at least 30, preferably at least 50. In general, the K-value does not exceed 120. Preferably, the K-value is from about 75 to about 95. As is well known, K-values as assigned to polyvinylpyrrolidone represent a function of the average molecular weight. K-values are derived from viscosity measurements and are calculated according to Fikentscher's formula.

Acrylic acid-containing polymers or methacrylic acid-containing polymers which may be employed include, but are not limited to, acrylic acid or methacrylic acid homopolymers, copolymers of acrylic acid or methacrylic acid and acrylic acid esters or methacrylic acid esters, and acrylic acid-containing or methacrylic acid-containing terpolymers, such as terpolymers including acrylic acid and acrylic acid esters and terpolymers of acrylic acid or methacrylic acid, butadiene, and styrene. In general, the acrylic acid-containing or methacrylic acid-containing polymer has adhesive properties.

In a preferred embodiment, the at least one acrylic acid-containing polymer or methacrylic acid-containing polymer is a polymer including an acrylic acid moiety or methacrylic acid moiety and at least one other moiety. Preferably, the at least one other moiety is water-insoluble.

In another embodiment, the at least one acrylic acid-containing or methacrylic acid-containing polymer is a copolymer of acrylic acid or methacrylic acid and an acrylic acid ester or methacrylic acid ester. In one embodiment, the ester is an acrylic acid ester. Acrylic acid esters which may be employed include, but are not limited to, ethyl acrylate, butyl acrylate, octyl acrylate, and 2-ethyl hexyl acrylate. The at least one acrylic-acid containing polymer which is employed in the composition, in one embodiment, may be a combination of two or more acrylic acid-containing copolymers of acrylic acid and the above-mentioned acrylic acid esters. In general, such copolymer has a molecular weight of from about 10,000 to about 5,000,000, preferably from about 10,000 to about 200,000.

In another preferred embodiment, the acrylic acid-containing polymer is a terpolymer including acrylic acid and two acrylic acid esters. The acrylic acid esters may be selected from those hereinabove described. In one embodiment, the terpolymer is a terpolymer of acrylic acid, butyl acrylate, and 2-ethyl hexyl acrylate. Examples of such terpolymers are sold by Monsanto as Gelva 2333, Gelva 2397, and Gelva 2484.

In another embodiment, the at least one acrylic acid-containing or methacrylic acid-containing polymer is a terpolymer of acrylic acid or methacrylic acid, butadiene, and styrene.

In a preferred embodiment, the acrylic acid-containing polymer or methacrylic acid-containing polymer, prior to mixing with the polyvinylpyrrolidone and the amine-containing polymer, is in the form of an emulsion. More preferably, the acrylic acid-containing polymer or methacrylic acid-containing polymer is in the form of an emulsion of a copolymer of acrylic acid or methacrylic acid and acrylic acid esters or methacrylic acid esters.

Amine-containing polymers which may be included in the composition include, but are not limited to, polyethyleneimine, amine-terminated polyethylene oxide, amine-terminated polyethylene/polypropylene oxide, polymers of dimethyl amino ethyl methacrylate, and copolymers of dimethyl amino ethyl methacrylate and vinyl pyrrolidone.

In one embodiment, the amine-containing polymer is polyethyleneimine. In general, the polyethyleneimine has a molecular weight of from about 25,000 to about 750,000, preferably from about 70,000 to about 750,000.

In general, the preparation of the adhesive composition takes place in an aqueous medium, whereby aqueous solutions of the polyvinylpyrrolidone and the amine-containing polymer are mixed with the emulsion containing the acrylic acid-containing or methacrylic acid-containing polymer.

Although the scope of the present invention is not to be limited to any theoretical reasoning, it is believed that the acid moieties in the acrylic acid-containing or methacrylic acid-containing polymer become co-crosslinked with the polyvinylpyrrolidone by the amine-containing polymer. Such reaction also is a competition reaction between the acid groups of the ring opened polyvinylpyrrolidone and the acid groups of the acrylic acid-containing polymer or methacrylic acid-containing polymer with the amine-containing polymer. In addition, the addition of the acrylic acid-containing polymer slows the rate of gelation of the polyvinylpyrrolidone by the polyamine. Thus, gelation of the resulting composition occurs over a period of minutes, as opposed to an almost instantaneous gelation. Therefore, one may use conventional coating equipment for forming the adhesive composition, and then drying the product.

The polyvinylpyrrolidone, acrylic acid-containing polymer or methacrylic acid-containing polymer and amine-containing polymer are present in amounts which enable co-crosslinking of the acid moieties of the polyvinylpyrrolidone and of the acrylic acid-containing polymer or methacrylic acid-containing polymer with the amine-containing polymer. In general, the polyvinylpyrrolidone and amine-containing polymer are present in the composition at a weight ratio of polyvinylpyrrolidone to amine-containing polymer of from about 40:1 to 150:1, preferably from about 60:1 to about 80:1, and the acrylic acid-containing polymer or methacrylic acid-containing polymer is present in the composition at a weight ratio of polyvinylpyrrolidone to acrylic acid-containing polymer or methacrylic acid-containing polymer of from about 8:1 to about 16:1, preferably from about 10:1 to about 16:1. Upon mixing of the above-mentioned components, an adhesive composition is formed which is not soluble in water, yet is capable of absorbing from about 3 to 10 times its own weight in water when dried. Such composition has improved tack or stickiness. The composition has a cohesiveness to itself which is greater than the adhesiveness to the object or body to which it is adhered. Thus, the adhesive may be peeled readily from the object or the body without damage or injury to the object or body.

In one embodiment, the composition further includes a plasticizer. Examples of plasticizers which may be employed include, but are not limited to, polyalkylene glycols such as polyethylene glycol and glycerine. Such plasticizers prevent drying of the adhesive and increase the tack. In one embodiment, the plasticizer is polyethylene glycol. The polyethylene glycol may have a molecular weight of from about 100 to about 600, preferably at about 300. The polyethylene glycol typically has a melting point of from about 20° C. to about 25° C. at a molecular weight of 600, and has a melting point below −10° C. at a molecular weight of 300. In general, the polyethylene glycol is added at a ratio of polyvinylpyrrolidone/polyethylene glycol of from about 0.5:1 to about 2:1, preferably from about 0.8:1 to about 1:1.

In another embodiment, the composition further includes a water-soluble tackifier. Examples of water-soluble tackifiers which may be employed include, but are not limited to, polyvinylethers such as polymethylvinylether and polyvinylpyrrolidone having no ring opened groups.

In yet another embodiment, the composition may further include a surfactant, such as a phospholipid surfactant or other surfactants that provide antibacterial stabilizing properties to the composition.

The composition of the present invention is useful in a wide variety of systems involving application to animal bodies, including especially human bodies. These include medical systems such as an adhesive for surgical drapes, wound and burn dressings and packings, bandages, plasters, transdermal drug delivery devices, and antimicrobial barriers for catheter hubs.

In a wound or burn dressing or packing, for example, in addition to the incorporation of a plasticizer and surfactant in the composition, the product may also contain a bactericide such as chlorhexidine gluconate, silver or copper compounds like silver sulfadiazine, silver apacide and copper apacide, or an antibiotic or other antimicrobial. The composition may also contain enough sodium chloride to match physiological saline in order to prevent osmotic pumping from the wound, and agents to promote regrowth of tissue. Wound or burn dressings and packings generally involve a releasable thermally formed plastic receptacles for holding the composition and a polymeric film, such as polyurethane film, backing to control moisture-vapor transmission.

The composition may be used to attach a medical device to the body. In this case the aqueous gel may contain, in addition to the tackifying plasticizer, an antimicrobial agent. When used as an adhesive to attach a catheter, such as a central venous catheter or intravenous catheter, it covers the hub providing an antimicrobial barrier to infection. The tacky composition may also be used to attach ostomy products to the body.

In a transdermal drug delivery system, the composition of the present invention will contain, in addition to the plasticizer, skin absorption agents like alcohols and amides, and at least one bioeffecting drug. Examples of drugs that may be incorporated in such a system are nitroglycerine, pilocarpine, scopolamine, clonidine, fentanyl, nicotine, fenfluramine, phenterimine, phenylpropanolamine, theophylline, lidocaine, benzocaine, capsaicin, nicotinates, ergotamine tartrate, miconazole nitrate, salicylates such as choline salicylate, methyl salicylate, and the like. Such drugs may be added to the composition in an amount up to about 10% by weight.

An electrolyte salt may be included in the composition to render it conductive for use in attaching electrocardiogram electrodes, transcutaneous electrical nerve stimulator electrodes, electro-surgical unit electrodes, biofeedback electrodes and iontophoresis drug delivery electrodes and defibrillation pads. Potassium chloride, sodium chloride, sodium acetate, and magnesium acetate are examples of suitable electrolyte salts. Such salts may be present in the composition in an amount between about 1 and about 20%, by weight, preferably about 2 and about 10%. The electrolyte salt may be incorporated in the reaction mixture at or about the time that the ring opened PVP and amine-containing polymer are mixed, preferably as by adding it to the water prior to dissolving the ring opened PVP. The conductive composition may also contain bioeffective material for iontophoresis drug delivery.

In addition, the electrolyte salts hereinabove described, as well as carbon black or metal powders such as copper powder, may be included in the adhesive composition to form a conductive adhesive, a static dissipative adhesive, or an anti-static adhesive for closure strips for the packaging of sensitive electronic components such as computer chips, for example, or of photographic and x-ray films. Such compositions possess adequate conductivity as well as good adhesiveness. Such an adhesive yet conductive composition also may be employed in clean room dirt removal mats, whereby the adhesive forms the top surface of the clean room mat, and retains dirt particles and metal particles.

The invention now will be described with respect to the examples; however, the scope of the present invention is not intended to be limited thereby.

EXAMPLE 1

A two-part system was made of Part A and Part B. Part A contained 50.35 g of a 20% wt./wt. polyvinylpyrrolidone solution (with ring opened pyrrolidone groups), 3.0 g potassium chloride, 24 g SDA40 ethyl alcohol and 1.25 g Gelva AE 259, which is an acrylic polymer but not having any acid groups present. Part B consisted of 12.0 g polyethylene glycol 300, 21.1 g SDA40 ethyl alcohol, and 1.40 g of a 12.5% solids solution of polyethyleneimine. The two parts were added to each other, mixed rapidly, and poured in the nip of a knife coater which had a release liner and a gap setting of 21 mils. Before the liner was pulled through fully, the gel had formed. The coated liner was then dried in an oven with high air flow at 110° C. The dried product was 2 mils thick, had good dry tack and had resistance of 10 ohms. The film, however, was not uniform because it gelled before being pulled through the nip.

EXAMPLE 2

A two-part system was made of Part A and Part B. Part A contained 50.41 g of a 20% polyvinylpyrrolidone solution wt/wt., 20 g of SDA40 ethyl alcohol, 3.0 g potassium chloride, and 1.30 g of Gelva 2484 (an acid containing acrylic acid ester adhesive) emulsion. Gelva 2484 is an acrylic acid ester and acrylic acid-containing terpolymer from Monsanto including acrylic acid, butyl acrylate, and 2-ethyl hexyl acrylate. Part B consisted of 12.12 g polyethylene glycol 300, 20 g of SDA40 ethyl alcohol and 1.27 g of 12.5% polyethyleneimine solution. The two parts were combined, mixed and poured into the nip of a knife over roller coater in which was a release liner, gap set for 21 mils. The liner was pulled through the coater. After removal, excess coating dripped for about 15 seconds before gelation started. The coating on the release liner was dried in an oven with high air flow at 110° C. for 5 minutes. The resulting 2 mil coating had excellent dry tack and good resistivity.

EXAMPLE 3

A two-part system was made of Part A and Part B. Part A contained 50.35 g 20% polyvinylpyrrolidone solution, 3 g potassium chloride, 25 g SPA40 ethyl alcohol and 1.30 g Gelva 2397 adhesive, which is an acrylic acid ester and acrylic acid-containing terpolymer having the components hereinabove described, and which has a higher acrylic acid content that Gelva 2484. Part B contained 12.12 g polyethylene glycol 300, 1.27 g 12.5% polyethyleneimine solution, and 20 g SDA40 ethyl alcohol. Parts A and B were combined, mixed and poured into the nip of a knife over a roll coater which had a release liner in the nip. The release liner was pulled through and the excess material dripped for more than 30 seconds before gelation started. The coating was dried in an oven with high air flow at 110° for 5 minutes. The 2 mil coating had excellent tack and resistivity.

EXAMPLE 4

A two-part system was made of Part A and Part B. Part A consisted of a mixture which was in a ratio of 50.34 g 20% polyvinylpyrrolidone (with partial ring opened groups), 25.31 g SDA40 ethyl alcohol and 1.30 g Gelva 2333 adhesive (an acrylic adhesive, including an acrylic acid ester and acrylic acid-containing terpolymer having the components hereinabove described, with an acid content between Gelva 2484 and Gelva 2397), and 3 g of potassium chloride. Part B was a mixture of 12.17 g polyethylene glycol 300, 1.27 g of a 12.5% solution of polyetheneneimine and 20.21 g SDA40 ethyl alcohol. The solutions of both parts were placed in separate tanks and were fed separately by two gear pumps to a static mixer (3 elements, 2½" long, ⅝" thick). The combined mixture was fed to the nip of a roll coater with a spreader bar through which a conductive release liner was passing. The width of the coater is 14" after the coater it went into a dryer oven with 3 zone heating and good air flow. The liner was being pulled at about 50 ft/min. At the exit of the dryer a second "easy release" liner was placed over the dried adhesive. The 14" wide web was slit to 3" wide and tested as a sealing tape for a package for electronic chips. It was found to have good adhesive properties and to prevent static charge build-up.

EXAMPLE 5

A two-part system was made of Part A and Part B. Part A contained 50.35 gms of a 20% polyvinylpyrrolidone with some ring opened pyrrolidone groups, 24 gms SDA40 ethyl alcohol, 1.03 gms of a 33% solution of polyvinyl methylether and 1.25 gms of Gelva AE259. Part B contained 12.0 gms polyethylenglycol, 25 gms of SDA40 ethyl alcohol, and 1.30 gms 12.5% polyethyleneimine. The two parts were mixed together, stirred, and then quickly poured into the nip of a knife over a roll coater with a gap of 21 mils and in which a release liner was placed. The liner was pulled through the gap and gelation occurred in the process of pulling. The coating on the release liner was placed in an oven with high air flow and heated at 110° C. It was dried for 15 minutes. After cooling it was tested for dry and wet tack. It had adequate dry tack but poor wet tack. The coating appeared to be non-uniform.

This illustrates the formation of a pressure-sensitive adhesive that does not contain any free acid groups in the backbone of the acrylic acid-containing polymer.

EXAMPLE 6

A two-part system was made of Part A and Part B. Part A contained 50.41 g of a 20% polyvinylpyrrolidone solution (containing ring opened pyrrolidone groups) 22 grams of SDA40 ethyl alcohol, 1.30 grams of Gelva 2484, and 1.24 g of a 20% solution of polymethylvinylether in water. Part B contained 12.18 g polyethylene glycol 300, 23 grams of SDA40 ethyl alcohol, and 1.10 grams of 12.5% polyethyleneimine. The two parts were combined, stirred and poured into the nip of a knife over a roller coater set at 21 mil gaps in which was a release liner. The liner with the coating was pulled through. Excess coating began to drip through the gap and after about 15 seconds began to gel.

The liner with the coating was placed in an oven with high air flow at 110° C. for 15 minutes. After cooling it was laminated to a thin film polyurethane of about 1 mil thickness. Samples were tested by removing the release liner from strips and dry and wet tack were determined. The sample was equivalent in dry tack to Example 5 but had much better wet tack.

EXAMPLE 7

A two-part system was made of Part A and Part B. Part A contained 50.35 grams of 20% polyvinylpyrrolidone, 23.60 grams SDA40 ethyl alcohol, 1.30 grams Gelva 2397 emulsion adhesive containing unneutralized acid groups in the backbone, and 1.56 g of a 20% solution of polymethylvinylether in water. Part B contained 12.12 grams of polyethylene glycol 300, 20 grams of SDA40 ethyl alcohol and 1.01 grams of a 12.5% polyethyleneimine in water. Part B was added to Part A and quickly stirred and added to the nip of a knife over a roll coater with a gap of 21 mils in which was a release liner. The liner was pulled through the gap depositing a film of the coating. After removal, excess coating dripped from the gap and did not start to gel for about 1 minute. The liner with the coating was placed in an oven with high air flow at 110° C. for 15 minutes. After removal it was allowed to cool and then laminated to a polyurethane film. A standard peel adhesion of this film with adhesive against stainless steel was measured at 350–500 grams. It had good adhesion to wet skin but was painlessly peeled from the skin.

EXAMPLE 8

A two-part system was made of Part A and Part B. Part A contained 49.83 grams 20% polyvinylpyrrolidone with partial ring opened pyrrolidone groups, 25.09 g SDA40 ethyl alcohol, and 1.58 g Gelva 2333 emulsion adhesive. Part B contained 1.27 g polyethyleneimine, 20.79 g SDA40 ethyl alcohol and 8.85 g polyethylene glycol 300. Part B was added to Part A, stirred and then quickly added to the nip of a knife over a roller coater, having a gap of 21 mils with a release liner in the gap. The release liner was pulled through and after it cleared the gap excess coating began dripping down. After about 30 seconds the coating solution began to gel. The coating on the release liner was placed in an oven with high air flow and at a temperature of 110° C. After 15 minutes the liner with the coating was removed and allowed to cool. It was laminated to a thin film urethane. It had good adhesion to the urethane film. Testing of the film laminated adhesive showed it had good adhesion to wet or damp skin but did not have as good dry tack as in Example 7.

EXAMPLE 9

Each of Formulations A, B, and C were made, having the following components:

|  | Part A |
|---|---|
| 50 g | 20% polyvinylpyrrolidone |
| 48 g | $H_2O$ |
| 1.3 g | 20% polymethylvinylether (PVM) in water |
| 0.08 g | sodium $C_{14}$–$C_{16}$ olefin sulfonate surfactant |
|  | Part B |
| 12 g | polyethylene glycol |
| 12 g | $H_2O$ |
| 1.0 g | 12.5% polyethyleneimine in $H_2O$ |

Formulation A had no adhesive component added. Formulation B further included 1.3 g of Gelva 2484 in Part A. Formulation C further included 1.3 g of Gelva 2333 in Part A.

For each formulation, Part B was added to Part A, and each formulation was stirred. Subsequent to stirring, each formulation was poured onto an interface of a wire wound stainless steel rod and glass. The rod then is rolled along the glass surface as the formulation is being applied, thereby forming a coating of each formulation on a glass surface. Each of Formulations A, B, and C then was dried at 105° C. for 15 minutes, and then covered with a polyester film. One-inch strips then were cut, and the adhesion of polyester to glass for each formulation was measured. The adhesion for each formulation was as follows:

Formulation A—1.1 oz./in.
Formulation B—3.7 oz./in.
Formulation C—4.5 oz./in.

It is to be understood, however, that the scope of the present invention is not to be limited to the specific embodiments described above. The invention may be practiced other than as particularly described above. The invention may be practiced other than as particularly described and still be within the scope of the accompanying claims.

What is claimed is:

1. A composition comprising a cross-linked salt of:
   (a) a polyvinylpyrrolidone having ring opened pyrrolidone groups;
   (b) at least one acrylic acid-containing or methacrylic acid containing polymer; and
   (c) an amine-containing polymer, wherein said polyvinylpyrrolidone and said amine-containing polymer are present in said composition at a weight ratio of polyvinylpyrrolidone to amine-containing polymer of from about 40:1 to about 150:1, and said acrylic acid-containing polymer or methacrylic acid-containing polymer is present in said composition at a weight ratio of polyvinylpyrrolidone to acrylic acid-containing polymer or methacrylic acid-containing polymer of from about 8:1 to about 16:1.

2. The composition of claim 1 wherein said polyvinylpyrrolidone has ring opened pyrrolidone groups which provide at least $1.5 \times 10^{-2}$ milliequivalents of carboxylic acid groups per gram of polymer.

3. The composition of claim 1 wherein said amine-containing polymer is selected from the group consisting of polyethyleneimine, amine-terminated polyethylene oxide, amine-terminated polyethylene/polypropylene oxide, polymers of dimethyl amino ethyl methacrylate, and copolymers of dimethyl amino ethyl methacrylate and vinyl pyrrolidone.

4. The composition of claim 3 wherein said amine-containing polymer is polyethyleneimine.

5. The composition of claim 1 wherein said polyvinylpyrrolidone has a K-value of at least 50.

6. The composition of claim 1 wherein said at least one acrylic acid-containing polymer or methacrylic acid-containing polymer is a terpolymer including acrylic acid and acrylic acid esters or a terpolymer including methacrylic acid and methacrylic acid esters.

7. The composition of claim 6 wherein said terpolymer is a terpolymer of acrylic acid, butyl acrylate, and 2-ethyl hexyl acrylate.

8. The composition of claim 1 wherein said at least one acrylic acid-containing polymer or methacrylic acid-containing polymer is a terpolymer of acrylic acid or methacrylic acid, butadiene, and styrene.

9. The composition of claim 1 and further comprising a plasticizer.

10. The composition of claim 9 wherein said plasticizer is selected from the group consisting of polyalkylene glycols and glycerine.

11. The composition of claim 10 wherein said plasticizer is polyethylene glycol.

12. The composition of claim 11, and further comprising a water soluble tackifying agent.

13. The composition of claim 12 wherein said tackifying agent is polymethylvinylether.

14. A hydrogel pressure sensitive adhesive for attaching a wound dressing to skin including the composition of claim 13.

15. A transdermal drug delivery system, said system including:
   (a) a hydrogel pressure sensitive adhesive including the composition of claim 13; and
   (b) at least one drug.

16. The composition of claim 12 wherein said tackifying agent is a polyvinylpyrrolidone having no ring opened pyrrolidone groups.

17. The composition of claim 1 and further comprising an electrolyte salt.

18. The composition of claim 17 wherein said electrolyte salt is selected from the group consisting of potassium chloride, sodium chloride, sodium acetate, and magnesium acetate.

19. The composition of claim 18 wherein said electrolyte salt is sodium acetate.

20. A conductive hydrogel pressure sensitive adhesive for closure strips employed in the packaging of electronic components, said adhesive including the composition of claim 18.

21. A conductive hydrogel pressure sensitive adhesive for attaching an electrode to skin including the composition of claim 18.

22. A conductive hydrogel pressure sensitive adhesive for a dirt removal mat for clean room use, said adhesive including the composition of claim 18.

23. A conductive hydrogel pressure sensitive adhesive for iontophoretic drug delivery devices including the composition of claim 18, and further including at least one bioeffective drug.

24. In a system for adhesion to an animal body or an object, wherein said system includes an adhesive, the improvement wherein said adhesive comprises the composition of claim 1.

25. The composition of claim 1 wherein said polyvinylpyrrolidone and said amine-containing polymer are present in said composition at a weight ratio of polyvinylpyrrolidone to amine-containing polymer of from about 60:1 to about 80:1.

26. The composition of claim 1 wherein said polyvinylpyrrolidone and said acrylic acid-containing polymer or said methacrylic acid-containing polymer are present in said composition at a weight ratio of polyvinylpyrrolidone to acrylic acid-containing polymer or methacrylic acid-containing polymer of from about 10:1 to about 16:1.

* * * * *